US008758831B2

(12) United States Patent
McNally et al.

(10) Patent No.: US 8,758,831 B2
(45) Date of Patent: *Jun. 24, 2014

(54) ANTIINFECTIVE FREE INTRAMAMMARY VETERINARY COMPOSITION

(75) Inventors: Vincent McNally, Sandyford (IE); James Patrick Morgan, Navan (IE); Bridie Morgan, legal representative, Navan (IE)

(73) Assignee: Bimeda Research & Development Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,391

(22) Filed: Jul. 8, 2011

(65) Prior Publication Data

US 2011/0268819 A1 Nov. 3, 2011

Related U.S. Application Data

(60) Division of application No. 12/410,092, filed on Mar. 24, 2009, now abandoned, which is a continuation of application No. 10/899,308, filed on Jul. 27, 2004, now abandoned, which is a continuation of application No. 10/304,093, filed on Nov. 26, 2002, now abandoned, which is a continuation of application No. 10/028,987, filed on Dec. 28, 2001, now Pat. No. 6,506,400, which is a continuation of application No. 09/694,676, filed on Oct. 24, 2000, now Pat. No. 6,340,469, which is a continuation of application No. 09/319,544, filed as application No. PCT/IE97/00085 on Dec. 17, 1997, now Pat. No. 6,254,881.

(30) Foreign Application Priority Data

Dec. 18, 1996 (IE) .......................................... 960896

(51) Int. Cl.
A61K 33/24 (2006.01)
A61P 29/00 (2006.01)

(52) U.S. Cl.
USPC ........................................................ 424/653

(58) Field of Classification Search
USPC ..................... 424/438, 407, 78.07; 514/504
See application file for complete search history.

(56) References Cited

U.S. PATENT DOCUMENTS

| 3,222,252 A | 12/1965 | Kraus |
| 3,912,806 A | 10/1975 | Dowrick et al. |
| 4,022,199 A | 5/1977 | Fetty |
| 4,049,830 A | 9/1977 | Pugliese |
| 4,073,920 A | 2/1978 | Dowrick |
| 4,113,854 A | 9/1978 | Andrews et al. |
| 4,172,138 A | 10/1979 | Rhodes |
| 4,344,967 A | 8/1982 | Easton et al. |
| 4,446,144 A | 5/1984 | von Daehne |
| 4,472,374 A | 9/1984 | Dowrick et al. |
| 5,017,369 A | 5/1991 | Marhevka |
| 5,195,966 A | 3/1993 | Corby |
| 5,593,384 A | 1/1997 | Halem |
| 6,107,344 A | 8/2000 | Loosemore |
| 6,254,881 B1 * | 7/2001 | McNally et al. ............. 424/438 |
| 6,340,469 B1 * | 1/2002 | McNally et al. ............. 424/438 |
| 6,506,400 B1 | 1/2003 | McNally et al. |
| 2004/0197422 A1 | 10/2004 | Dorgan |

FOREIGN PATENT DOCUMENTS

| EP | 0 081 896 A2 | 6/1983 |
| EP | 0 271 306 A2 | 6/1988 |
| EP | 0 971 690 B1 | 1/2000 |
| GB | 0 792 545 | 3/1958 |
| GB | 1 312 918 | 4/1973 |
| GB | 1 441 747 | 7/1976 |
| GB | 1 456 349 | 11/1976 |
| GB | 2 273 655 A | 6/1984 |
| GB | 2 273 441 A | 6/1994 |
| GB | 2 273 443 A | 6/1994 |
| GB | 2273441 A * | 6/1994 ................... 424/438 |
| JP | 05-301818 A | 11/1993 |
| JP | 08-020543 A | 1/1996 |
| JP | 08-291049 A | 11/1996 |
| JP | 10-512605 T | 12/1998 |
| RU | 2 028 798 C1 | 2/1995 |
| WO | WO 94/13261 | 6/1994 |
| WO | WO 95/31180 | 11/1995 |
| WO | WO 96/17615 A1 | 6/1996 |
| WO | WO 96/23581 A1 | 8/1996 |

OTHER PUBLICATIONS

Meaney, W.J.,"Dry period teat seal on bovine udder infection", Ir. J agric. Res. 16: 293-299 (1977).*
Osmonds Teat Seal, submitted to the European Patent Office with an Opposition filed Jun. 4, 2003, against corresponding European Patent No. EP 0 971 690, which issued from European Patent Application No. 97949079.4 (4 pages).
ProAgri, http://www.proagri.co.za/uitgawe_07/7-05_Cloxamasteh.htm, Sep. 1996 (9 pages).

(Continued)

Primary Examiner — Daniel Sullivan
Assistant Examiner — Ping Cao
(74) Attorney, Agent, or Firm — Finnegan, Henderson, Farabow, Garrett & Dunner LLP

(57) ABSTRACT

An antiinfective-free formulation for prophylactic treatment of mastitis in dry cows comprises a seal formulation having approximately 65% by weight of bismuth sub-nitrate in a gel based on aluminum stearate. The seal formulation is prepared by adding the bismuth sub-nitrate to the gel base in at least two separate stages.

15 Claims, No Drawings

(56) References Cited

OTHER PUBLICATIONS

Merck Index, 13th Edition, 2001, pp. 356, 1251, 1269, and 1293 (4 pages).
Excerpts from "Le Grand Dictionnaire Terminologique": "antibiotique" and "anti-infectieux," Aug. 12, 2005 (4 pages).
Merck Index, 13th Edition, 2001, p. 23 (1 page).
Bradley, A.J., "A Study of the Anti-Infective Properties of TeatSeal™ Formulations in the Presence and Absence of Acriflavine," submitted on Feb. 12, 2007, to the Board of Appeals of the European Patent Office for Case No. T 0028/06-3302 in connection with an Opposition against corresponding European Patent No. EP 0 971 690, which issued from European Patent Application No. 97949079.4 (6 pages).
Curriculum vitae of Dr. Andrew John Bradley, Jan. 10, 2009 (3 pages).
Smith, A., Neave, F.K., Jones, A. and Gore, D.N. The persistence of cloxacillin in mammary gland when infused immediately after the last milking of the lactation. J. Dairy Res. 34: 47, 1967.
Meaney, W.J. and O'Shea, J., *Moorepark 25th Anniversary Publication. II. Animal Health and Machine Milking*, Dep. Dairy Husbandry, Moorepark Res. Cent., Fermoy, Co. Cork, Irish Republic, pp. 249-265, 1986.
Osmonds Teat Seal NA Product Information, 2003, http:www.osmonds.ie/intra.htm, Oct. 26, 2009.
Patentee, Letter concerning EPO Appeal No. T1133/09-3302, dated Mar. 26, 2010 (12 pages).
Meaney, W.J., First Declaration in Appeal No. T1133/09-3302; European Patent No. 0971690, in the name of Bimeda Research & Development Ltd., dated Mar. 25, 2010 (2 pages).
Annex 1 to First Declaration of W. J. Meaney, curriculum vitae, dated Feb. 15, 2010 (7 pages).
Opponent, Notice of Opposition to EP0971690, dated May 27, 2003 (36 pages).
Opponent, Notice of Opposition to EP0971690, dated Jun. 4, 2003 (60 pages).
Patentee, Letter concerning EP0971690 Notices of Opposition, Application No. 97 949 079.4, dated Feb. 17, 2004 (4 pages).
EPO oral proceedings summons and annex, Application No. 97 949 079.4, dated Dec. 15, 2004 (8 pages).
Opponent, Letter concerning Opposition to EP0971690, Application No. 97 949 079.4, dated Sep. 15, 2005 (2 pages).
Minutes of oral proceedings before the Opposition Division of the European Patent Office, Application No. 97 949 079.4, dated Oct. 27, 2005 (5 pages).
EPO Board of Appeals Decision Revoking EP0971690, dated Nov. 11, 2005 (18 pages).
Patentee, Statement of Grounds of Appeal and attachments concerning EPO Appeal No. T 0028/06-3302, dated Mar. 10, 2006 (32 pages).
Opponent, Letter concerning Opposition to EP0971690, Application No. 97 949 079.4, dated Jul. 3, 2006 (5 pages).
Opponent, Letter concerning EPO Appeal No. T 0028/06-3302, dated Jul. 27, 2006 (10 pages).
Patentee, Letter and attachments concerning EPO Appeal No. T 0028/06-3302, dated Feb. 12, 2007 (47 pages).
Patentee, Letter and attachment concerning EPO Appeal No. T 0028/06-3302, dated Mar. 14, 2007 (6 pages).
Patentee, Letter concerning EP0971690 Opposition proceeding, dated Feb. 26, 2008 (7 pages).
Summons to attend oral proceedings and annex, Application No. 97 949 079.4, dated Aug. 26, 2008 (5 pages).
Patentee, Letter concerning EP0971690 Opposition proceeding, Application No. 97 949 079.4, dated Jan. 12, 2009 (4 pages).
Minutes of oral proceedings before the Opposition Division of the European Patent Office, Application No. 97 949 079.4, dated Mar. 27, 2009 (5 pages).
Patentee, Statement of Grounds of Appeal and attachments concerning EPO Appeal No. T 1133/09-3302, dated Aug. 6, 2009 (64 pages).
Brady, P. D., Witness Statement in the matter of European Patent No. 0971690 in the name of Bimeda Research and Development Ltd., under Opposition, dated Feb. 16, 2010 (1 page).
Draper R., Witness Statement in the matter of European Patent No. 0971690 in the name of Bimeda Research and Development Ltd., under Opposition, dated Feb. 16, 2010 (40 pages including accompanying exhibits).
Meaney, W.J., Report on Field Trial to Compare the Efficacy of Teat Seal and Teat Seal Containing 0.1% Acriflavine after Experimental Challenge with *Streptococcus dysgalactiae* in Nonlactating Dairy Cows, dated Feb. 16, 2010 (6 pages).
Patentee, Letter concerning field trial, Appeal No. T 1133/09-3302, dated Feb. 17, 2010 (7 pages).
Stableforth, A.W., et al., Entozon and Acriflavine for the Treatment of Chronic, Contagious Bovine Mastitis, The Veterinary Record, Jun. 4, 1938, pp. 663-676, vol. 50, No. 23.
Johnson, S.D., Observations on the Treatment of Mastitis with Acriflavine, Cornell Vet., 1941, pp. 127-148, 31:127.
Papers submitted in opposition proceedings in counterpart European Patent No. 076068, 72 pages.
"Acriflavine," definition from Answers.com, http://www.answers.com/topic/acriflavine, 1 page, Jul. 23, 2010.
Meaney, W.J., "Dry period teat seal", Vet. Rec. (1976).
Meaney, W.J., "Effect of a Dry period teat seal on bovine udder infection", Ir. J. agric. Res. 16: 293-299 (1977).
Farnsworth, R.J., "Use of a teat sealer for prevention of intramammary infections in lactating cows", *Jayma*, vol. 177, No. 5, pp. 441-444 (1980).
Robert, P., *Dictionnaires Le Robert*, (1993).
Block, S., "Disinfection, Sterilization, and Preservation," *Lea & Febiger*, Third Edition, pp. 346-398, (1983).
León-Barùa, et al., "In vitro and In vivo effects of three bismuth compounds on fermentation by colonic bacteria", *Rev. of Infectious Diseases*, 12:1 S24-S29, Jan.-Feb. 1990.
Vogt, K., et al., "The minimum inhibitory concentrations of various bismuth salts against *Campylobacter pylori*", Zbl. Bakt. 271:304-310 (1989).
Kirk, R., et al., "Encyclopedia of Chemical Technology", *The Interscience Encyclopedia, Inc.*, 2:77-84 and 538-540 (1948).
Kollidon, "Polyvinylpyrrolidone for the pharmaceutical industry", BASF, pp. 18-21 (1996).
Berry, E.A. et al., "The effect of an intramammary teat seal on new intramammary infections", J. Dairy Sci., 85:2512-2520 (2002).
"Dorland's Illustrated Medical Dictionary," p. 19, © 1994 by W.B. Saunders Co., 3 pages.
"The Merck Veterinary Manual," Seventh Ed., 1991, p. 1532, 2 pages.
Blood, D.C. et al., "Bailliere's Comprehensive Veterinary Dictionary," p. 11, © 1988 Bailliere Tindall, 4 pages.
Tawil, G.G., et al., "Bacteriostatic and Bactericidal Activities of Acriflavine-Antibiotic Combinations," Scientia Pharmaceutica (Sci. Pharm.) 54, 19-22 (1986), © Osterreichische Apotheker-Verlagsges, m.b.H., Wien, Printed in Austria.
European Patent Office, Board of Appeals, "Decision of the Technical Board of Appeal 3.3.02 of Mar. 21, 2007", Case No. T 0028/06-3.3.02, Appellant: Bimeda Research & Development Limited, 18 pages.
McArthur, B.J. et al., "Efficacy of a Latex Teat Sealer," Journal of Dairy Science (1984), vol. 67 No. 6, pp. 1331-1335.
"Guide to the Japanese Pharmacopoeia," Twelfth edition, first div. official monographs, Hirokawa Shoten Limited (1991), C-1149-1153.
Drug additives dictionary, Yakuji Nippo Limited (1994). p. 71.
Drug additives dictionary, Yakuji Nippo Limited (1994), p. 148.
Excerpts from "Dictionnaire de Médecine Flammarion": "antibiotique" and "antiseptique," "infectieux," "infection," @ 1975, 1982, 1989 text and illustration by Flammarion, (6 pages).
Excerpts from "Le Nouveau Petit Robert": "antibiotique," @ Dictionnaires Le Robert, 1993 pour Le Nouveau Petit Robert, édition entièrement revue et amplifiée due Petit Robert. (3 pages).
"Cours National de Pharmacologie," Chapter 2.18.11, © 1983 Edition Marketing, (16 pages).
Excerpts from "Dictionnaire Médical": "antibiotique" and "anti-infectieux," © Masson, Paris, 1999, 2001, (5 pages).

(56) References Cited

OTHER PUBLICATIONS

Meaney, W.J. et al., "New Opportunities in Dry Cow Therapy" National Mastitis Council Annual Meeting Proceedings (2003), pp. 50-59.
Huxley, J.N. et al., "Evaluation of the Efficacy of an Internal Teat Sealer During the Dry Period," J. Dairy Sci., vol. 85, pp. 551-561, © American Dairy Science Association (2002).
Extract from 27th Edition Dorland's Illustrated Medical Dictionary (1988), pp. 98 and 102, (3 pages).
Article from Pro Agri and Unverified English translation of article from Pro Agri, Sep. 1996, (11 pages).
Decision of the Opposition Division of the European Patent Office dated Mar. 27, 2009, Application No./Patent No. 97 949 079.4-2108/971690, Decision Revoking the European Patent, (17 pages).
First Declaration of Dr. Andrew Bradley dated Jan. 10, 2009, (7 pages).
Blowey, R. et al., "Mastitis Control in Dairy Herds," (1995), pp. 29-30, © Farming Press, Ipswich, (3 pages).
Pearson, J.K.L., "The Use of Penicillin in the Prevention of C. pyogenes Infection of the Non-Lactating Udder," The Veterinary Record, (Mar. 25, 1950), vol. 62, No. 12, pp. 166-168.
Pearson, J.K.L., "Further Experiments in the Use of Penicillin in the Prevention of C. pyogenes Infection of the Non-Lactating Bovine Udder," The Veterinary Record, (Mar. 24, 1951), vol. 68, No. 12, pp. 215-220.
Smith, A. et al., "Methods of Reducing the Incidence of Udder Infection in Dry Cows," The Veterinary Record, (Nov. 11, 1967), pp. 504-510.
Blowey, R. et al., "Mastitis Control in Dairy Herds," (1995), Chapter 1, Introduction, p. 1, © Farming Press, Ipswich, (2 pages).
Clegg, F.G., et al., "Dry Cow Therapy: A Comparative Field Trail Using Benzathine Cloxacillin and Erythromycin," British Veterinary Journal (1975), vol. 131, No. 6, pp. 639-642.
Boddie, R.L. et al., "Dry Cow Therapy: Effects of Method of Drug Administration on Occurrence of Intramammary Infection," Journal of Dairy Science (1986), vol. 69, No. 1, pp. 253-257.
Smith, K.L., et al., "Environmental Pathogens and Intramammary Infection During the Dry Period," Journal of Dairy Science (1985), vol. 68, No. 2, pp. 402-417.
Hogan, J.S., et al., "Efficacy of Dry Cow Therapy and a Propionibacterium Acnes Product In Herds with Low Somatic Cell Count," Journal of Dairy Science, vol. 77, No. 11, pp. 3331-3337.
Williamson, J.H., et al., "The Prophylactic Effect of a Dry-Cow Antibiotic Against *Streptococcus uberis*," New Zealand Veterinary Journal (1995), vol. 43, No. 6, pp. 228-234.
"Council Directive 92/46/EEC of Jun. 16, 1992 Laying Down the Health Rules for the Production and Placing on the Market of Raw Milk, Heat-Treated Milk and Milk-Based Products," Official Journal L 268,Sep. 14, 1992, pp. 0001-0031, (34 pages).
Boyer, P.J., "Outbreak of Clinical Mastitis in Dairy Cows Following 'Blitz' Therapy," (Letter), The Veterinary Record, (Jul. 12, 1997), vol. 141, No. 2, p. 55.
Edmondson, P.W., "Clinical Mastitis in Dairy Cows After 'Blitz' Therapy," (Letter), The Veterinary Record (Jul. 26, 1997), vol. 141, No. 4, p. 108.
Huxley, J.N., et al., "Practical Usage of an Internal Teat Sealer," Proceedings of the British Mastitis Conference (2002) Brockworth, pp. 92-93, Institute for Animal Health/Milk Development Council.
Woolford, M.W., et al., "The Prophylactic Effect of a Teat Sealer on Bovine Mastitis During the Dry Period and the Following Lactation," New Zealand Veterinary Journal 46 (1998), pp. 12-19.
Meaney W.J., et al., "The Use of a Non-Antibiotic Teat Sealer in Combination with a Food-Grade Bacteriocin, Lacticin 3147, for Mastitis Prevention In Non-Lactating Dairy Cows," Cattle Practice (BCVA 1999), vol. 7, Part 2, pp. 215-219.
Berry, E.A., "To Dry Cow Treat or Not?" Proceedings of the British Mastitis Conference (2000), Institute of Animal Health/Milk Development Council, Shepton Mallet, Somerset, UK, pp. 37-43.
Green, M.J., et al., "Influence of Dry Period Bacterial Intramammary Infection on Clinical Mastitis in Dairy Cows," Journal of Dairy Science, vol. 85, No. 10, pp. 2589-2599, © American Dairy Science Association (2002).

\* cited by examiner

ANTIINFECTIVE FREE INTRAMAMMARY VETERINARY COMPOSITION

PRIORITY

This application is a divisional of U.S. patent application Ser. No. 12/410,092, filed Mar. 24, 2009 now abandoned, which is a continuation of U.S. patent application Ser. No. 10/899,308, filed Jul. 27, 2004, now abandoned, which is a continuation of U.S. patent application Ser. No. 10/304,093, filed Nov. 26, 2002, now abandoned, which is a continuation of U.S. patent application Ser. No. 10/028,987, filed Dec. 28, 2001, now U.S. Pat. No. 6,506,400, which is a continuation of U.S. patent application Ser. No. 09/694,676, filed Oct. 24, 2000, now U.S. Pat. No. 6,340,469, which is a continuation of U.S. patent application Ser. No. 09/319,544, filed Aug. 10, 1999, now U.S. Pat. No. 6,254,881, which is an entry into the national stage under 35 U.S.C. §371 of International PCT Application No. PCT/IE97/00085, filed Dec. 17, 1997, each of which is incorporated by reference in their entirety.

INTRODUCTION

The invention relates to a veterinary composition, particularly for the prophylactic treatment of mastitis in cows.

Bacterial infection via the teats of a cow is the most common cause of mastitis.

It is known to treat teats of a cow with a long acting antibiotic in a slow release form with effective cover only being provided whilst minimum inhibitory concentration (MIC) levels of the antibiotic are maintained. This period of cover can vary from 4 to 10 weeks.

It is also known to infuse a cloxacillin-based antibiotic into the udder following the last lactation and before the cow is dried off, immediately followed by a seal formation to seal the teat canal.

The invention is directed towards providing an improved veterinary composition, particularly for the prophylactic treatment of mastitis in dry cows.

STATEMENTS OF INVENTION

We have found that if a physical barrier is provided within the teat canal and/or the lower teat sinus during the dry period without the use of antibiotics, the incidence of mammary disorders is substantially reduced. This is very surprising as all conventional treatments involve the use of antibiotics. Because no antibiotics are required very substantial advantages result, without any significant reduction in effectiveness.

We have found that if a physical barrier is provided within the teat canal and/or the lower teat sinus during the dry period without the use of antibiotics, the incidence of mammary disorders is substantially reduced. This is very surprising as all conventional treatments involve the use of antibiotics. Because no antibiotics are required very substantial advantages result, without any significant reduction in effectiveness.

According to the invention there is provided an antiinfective-free formulation for prophylaxis of intramammary infection comprising a seal formulation to provide a physical barrier in the teat canal.

This non-antibiotic approach to preventing new dry period infection in dairy cows has major potential for the dairy industry as it results in the reduction of the incidence of antibiotic contamination in early season milk production. Thus the invention provides a quality improvement to dairy production and will facilitate farmers meeting consumer preferences for reducing the level of antibiotics used in food production.

According to another aspect the invention provides an antiinfective-free method of prophylactic treatment of mammary disorders in non-human animals during an animal's dry period by sealing the teat canal with a seal formulation to provide a physical bather in the teat canal.

The invention also provides a prophylactic method of controlling the infection of the mammary gland by a mastitis-causing organism by sealing the gland with a seal formulation to provide a physical bather in the teat canal.

In a particularly preferred embodiment of the invention the seal formulation comprises a non-toxic heavy metal salt in a gel base. Preferably, the heavy metal salt is present in an amount of between 50% and 75% by weight, most preferably approximately 65% by weight. We have found that these are the optimum levels of heavy metal salt to achieve an effective seal.

In a preferred embodiment of the invention the heavy metal salt is bismuth subnitrate. This is a particularly useful non-toxic heavy metal salt.

In one embodiment of the invention the base is a gel based on aluminium stearate. Preferably, in this case, the gel includes a vehicle such as liquid paraffin. This formulation has effective processing and use properties.

In another embodiment of the invention the gel comprises a polyethylene gel. The gel may be based on low density polyethylene or on high density polyethylene.

The invention also provides a veterinary composition for use in the prophylactic treatment of mammary disorders in non-human animals during an animal's dry period.

According to a further aspect the invention provides a process for preparing a seal formulation comprising the steps of adding a non-toxic heavy metal salt to a gel base in at least two separate stages. This process is particularly effective for producing the preferred seal formulation of the invention.

Preferably, a first portion of heavy metal salt is added to a gel base in a first stage and a second portion of the heavy metal salt is added to the gel base containing the first portion of the heavy metal salt.

In this case preferably the weight ratio of the second portion of the heavy metal salt to the first portion of the heavy metal salt is at least 1:1, most preferably approximately 2:1.

DETAILED DESCRIPTION OF INVENTION

The invention will be more clearly understood from the following description thereof given by way of example only.

Example 1

Raw materials:
liquid paraffin B.P. 434.8 Kg
Alugel 30 DF (Sterile) 69.2 Kg
Bismuth Sub-Nitrate 936.0 Kg
B.P.C. (Sterile)

To prepare a batch of seal formulation the liquid paraffin is first delivered into a Skerman 800 L kettle. The mixer is run at 20 RPM. The Alugel 30 DF (aluminium stearate) is then added through the transfer port. The mixer is turned off between additions of the Alugel powder. The steam line is opened and the temperature is allowed to rise to 160 to 165° C. This temperature is held for approximately 2 hours to sterilise the mixture. At the end of the sterilising cycle, the condensate valve is opened and blown down. Cooling water is then allowed into the jacket to cool the contents to less than 40° C. The base thus formed is then checked for quality. If necessary, the batch base may be homogenised for 10 minutes using a Silverson Homogeniser.

The charge port is then opened and 296 kg of the bismuth sub-nitrate is added in 10 kg lots. The contents are mixed for one minute at 20 RPM between additions of each 10 kg of bismuth sub-nitrate. Mixing is continued for approximately 1 hour at 45 RPM.

The remaining 640 Kg of bismuth sub-nitrate is then added in 10 Kg lots as above and mixing is continued for 1 hour following the final additions.

We have found that the addition of the bismuth sub-nitrate in two separate portions is important in producing a seal which can be processed and used effectively.

If necessary, the mixer is homogenised for 15 minutes using a Silverson Homogeniser.

The product is then transferred to a Colibri filling machine for filling into injector tubes.

Example 2

5 cows were infused in all four quarters at drying off with the seal formulation prepared as described in Example 1. These cows had previously been determined as uninfected in all four quarters.

Commencing at the first milking after calving, these cows were milked and the composite milk sample collected for analysis. This process was repeated for the first 10 makings after calving. Milk samples were also collected in the same manner from 5 untreated cows.

To simulate the milk handling process within the milking system, these milk samples were passed through a fibre filter material used in milking machine filters. The milk samples were then analysed by mass spectrometry for bismuth concentration.

The average bismuth level in milk drawn at first milking was 3.3 ppm declining to 0.39 ppm at milking No. 10. The maximum level recorded for any individual cow was 8 ppm at first milking. For untreated cows the levels fluctuated in the range 0.001 to 0.03 ppm.

The seal formulation described in Example 1 was administered at drying off and has been shown to reduce the incidence of new infection in the dry cow period and in the period around calving. The reduction appears to be comparable with that achieved by prophylactic antibiotic treatment. Thus, the seal of the invention very surprisingly offers a non-antibiotic approach to dry cow period prophylaxis.

Example 3

Evaluation of seal of Example 1

4 Mastitis-free cows selected at drying off.
2 Teats in each cow infused at drying-off with seal and remaining teats untreated (day 0).
8 Teats sealed and 8 teats untreated (controls).
3 Days later (day 3) all, teats were inoculated into the teat canal (depth of 4 mm; using 22 cfu of Streptococcus dysgalactiae code M and an inoculum volume of 0.1 ml).
New infections resulting from use of the inoculum occurred in five (5) of the untreated quarters in the period day 3 to day 13.
New infections resulting from use of the inoculum occurred in two (2) of the treated quarters in the period day 3 to day 13.
Resulting new infections were monitored daily for 10 consecutive days after inoculation (today 13).
Samples of secretion were collected in an aseptic manner from quarters showing signs of clinical mastitis prior to treatment with antibiotics.
All quarters in all 4 cows were sampled in an aseptic manner on day 13 (the last day of the trial)—these samples were used to:
(1) check the amount of seal remaining in teats
(2) monitor the level of $Str.$ $dysgalactiae$ surviving in the teats after 10 days Clinical Infection Results

| CFU/ml | Inoculation Depth | Control | Seal |
|---|---|---|---|
| 22 | 4 mm | $5^a/8^b$ 63% | $2^a/8^b$ 25% |

[a]Number of new infections
[b]Number of quarters challenged with $Str.$ $dysgalactiae$ Example 4

Evaluation of seal of Example 1

17 Mastitis-free cows* selected at drying off
2 Teats in each cow infused at drying-off with seal and remaining teats untreated (day 0).
32 Teats sealed and 32 teats untreated (controls).
3 Days later (day 3) all teats were inoculated into the teat canal (depth of 17 mm; using 1,190 cfu of $Streptococcus$ $dysgalactiae$ code M and an inoculum volume of 0.1 ml).
New infections resulting from use of the inoculum occurred in twenty (20) of the untreated quarters in the period day 3 to day 13.
New infections resulting from use of the inoculum occurred in eight (8) of the treated quarters in the period day 3 to day 13.
Resulting new infections were monitored daily for 10 consecutive days after inoculation (to day 13).
Samples of secretion were collected in an aseptic manner from quarters showing signs of clinical mastitis prior to treatment with antibiotics.
All quarters in all 17 cows were sampled in an aseptic manner on day 13 (the last day of the trial)—these samples were used to:
(1) check the amount of seal remaining in teats
(2) monitor the level of $Str.$ $dysgalactiae$ surviving in the teats after 10 days Clinical Infection Results

| CFU/ml | Inoculation Depth | Control | Seal |
|---|---|---|---|
| 1,190 | 17 mm | $20^a/32^b$ 63% | $8^a/32^b$ 25% |

[a]Number of new infections
[b]Number of quarters challenged with $Str.$ $dysgalactiae$
* A total of 4 quarters were infected in three cows and these quarters were excluded from the study. Therefore 32 quarters were assigned to each treatment.

Example 5

A total of 528 cows in three commercial herds were used. Each herd had a general history of dry period mastitis. The breed of the herds was predominately Fresian or Fresian Crosses.

Cows with at least three uninfected quarters, immediately prior to drying off, were identified within the three herds. All individual quarters were assumed to be independent units. The treatments: used were as follows.

1. Negative Control-Untreated, no infusions at drying off, but teat ends were sanitised with alcohol soaked cotton wool swabs.

off is very surprisingly equivalent in terms of prophylactic efficacy, to a long acting dry cow antibiotic. All three treatments reduced new IMI during the dry period by approximately 85%. Surprisingly, there was no significant difference between the antibiotic based treatments and the antibiotic-free treatment of the invention. Thus, this study has shown that by physically sealing the teat canal with a seal which has no bacteriostatic or bacterial action, the dry period IMI may, surprisingly, be controlled. The invention has the potential therefore of achieving dry period prophylaxis on a wide scale, at a lower unit cost, and with no risk of antibiotic residues after calving.

The invention is not limited to the embodiments hereinbefore described which may be varied in detail.

TABLE 1

New intramammary infections (IMI) identified during the study, grouped by period and by herd.
(Within a row, values with differing superscripts are significantly different)

Number of new IMI (quarters)

| | 1. Negative controls | | | 2. Positive controls | | | 3. Antibiotic + Seal | | | 4. Seal | | |
|---|---|---|---|---|---|---|---|---|---|---|---|---|
| Herd ID | 1 | 2 | 3 | 1 | 2 | 3 | 1 | 2 | 3 | 1 | 2 | 3 |
| Total no quarters DRY PERIOD | 249 | 141 | 138 | 249 | 141 | 138 | 249 | 141 | 139 | 249 | 141 | 138 |
| Clinical IMI | 10 | 6 | 2 | 0 | 1 | 1 | 1 | 1 | 0 | 1 | 0 | 0 |
| CALVING IMI | | | | | | | | | | | | |
| Strep. Spp. | 25 | 21 | 4 | 0 | 4 | 1 | 2 | 1 | 1 | 2 | 2 | 0 |
| S. aureus | 1 | 2 | 0 | 0 | 0 | 0 | 0 | 0 | 0 | 0 | 1 | 0 |
| Coag. Neg. staph. | 2 | 0 | 4 | 0 | 0 | 1 | 1 | 0 | 1 | 4 | 0 | 2 |
| Coliforms | 1 | 2 | 1 | 1 | 2 | 1 | 1 | 0 | 0 | 0 | 1 | 0 |
| Other organisms | 0 | 2 | 0 | 1 | 1 | 0 | 0 | 1 | 0 | 0 | 0 | 0 |
| Clinical, no growth | 1 | 1 | 0 | 0 | 0 | 0 | 0 | 0 | 0 | 0 | 0 | 0 |
| Total calving IMI | 30 | 28 | 9 | 2 | 7 | 3 | 4 | 2 | 2 | 6 | 4 | 2 |
| Total IMI | 40 | 34 | 11 | 2 | 8 | 4 | 5 | 3 | 2 | 7 | 4 | 2 |
| Overal IMI rate (%) | 16.1 | 24.1 | 8.0 | 0.8 | 5.7 | 2.9 | 2.0 | 2.1 | 1.4 | 2.8 | 2.8 | 1.4 |
| Total IMI across herds & periods Strep. Spp. IMI | | $68^a$ | | | $7^b$ | | | $6^b$ | | | $5^b$ | |
| Other paths IMI | | $17^c$ | | | $7^d$ | | | $4^d$ | | | $6^d$ | |
| All paths IMI | | $85^f$ | | | $14^g$ | | | $10^g$ | | | $13^g$ | |
| Total quarters | | 528 | | | 528 | | | 528 | | | 528 | |
| Overall new IMI Rate | | 16.1% | | | 2.7% | | | 2.5% | | | 1.9% | |

2. Positive Control-treated with 250 mg cephalonium in a long-acting base, infused at drying off. This product is known as CEPRAVIN DRYCOW. Cepravin is a trademark of Mallinckrodt Veterinary.
3. Antibiotic with Seal-Cloxacillin benzathine 600 mg in a 4 g unit dose infused at drying off and followed immediately by an infusion of 4 g of a blend of bismuth sub-nitrate (66%) in liquid paraffin with 8.5% Alugel 30 DF.
4. Seal—Bismuth sub-nitrate 66% w/w in liquid paraffin with 8.5 alugel 30 DF in a unit dose of 4 g infused at drying off.

These treatments were randomised among the 528 cows determined to have three of four uninfected quarters at drying off. The treatments were randomised between quarters to achieve as far as possible the same number of quarters per treatment, left and right, front and back.

Bacteriological results for individual quarters at drying off and at calving were compared to calculate the incidence of new intramammary infections (IMI). Chi-square testing was used to compare the incidence of the new infection between quarters, treatments and controls.

The results of the treatments are summarised in Table 1.

This experiment has demonstrated that the antinfective-free seal formulation of the invention administered at drying

The invention claimed is:

1. A method of prophylactic treatment of mammary disorders in non-human animals during an animal's dry period, the method comprising:
   preparing a seal formulation by:
      combining liquid paraffin with aluminum stearate to form a gel base,
      adding a first portion of bismuth sub-nitrate to the gel base, and
      adding a second portion of bismuth sub-nitrate to the first portion and the gel base after a first period of time elapses following the addition of the first portion to form the seal formulation, the first period of time being at least one hour; and
   injecting the seal formulation into the teat of the animal.

2. The method of claim 1, wherein preparing the seal formulation further includes:
   heating the gel base to sterilize the gel base; and
   cooling the heated gel base before adding bismuth sub-nitrate to the gel base.

3. The method of claim 2, wherein the gel base is heated for at least 2 hours.

4. The method of claim 2, wherein the gel base is heated to 160° C. or higher, and cooled to 40° C. or lower.

5. The method of claim 1, wherein the first portion of bismuth sub-nitrate and the gel base are continuously mixed during the first period of time.

6. The method of claim 1, wherein preparing the seal formulation further includes waiting a second period of time after adding the second portion of bismuth sub-nitrate before injecting the seal formulation.

7. The method of claim 6, wherein the second period of time is at least one hour.

8. The method of claim 6, wherein the first and second portions of bismuth sub-nitrate and the gel base are continuously mixed during the second period of time.

9. The method of claim 1, wherein the gel base is homogenized before adding bismuth sub-nitrate.

10. The method of claim 1, wherein the aluminum stearate is provided as a powder.

11. The method of claim 1, wherein a weight ratio of the second portion to the first portion is at least 1:1.

12. The method of claim 11, wherein the weight ratio of the second portion to the first portion is at least 2:1.

13. The method of claim 1, wherein the seal formulation is injected during the animal's dry period.

14. The method of claim 1, wherein the seal formulation consists essentially of the gel base and bismuth sub-nitrate.

15. The method of claim 1, wherein the seal formulation is injected in unit doses of approximately 4 grams at drying off.

\* \* \* \* \*